United States Patent [19]

Ueda et al.

[11] Patent Number: 4,786,649
[45] Date of Patent: Nov. 22, 1988

[54] ANTIMICROBIAL 1-THIENYL-4-OXOQUINOLINE-3-CARBOXYLIC ACIDS

[75] Inventors: Hiraki Ueda; Hisashi Miyamoto, both of Tokushima, Japan

[73] Assignee: Otsuka Pharmaceutical Company Limited, Tokyo, Japan

[21] Appl. No.: 929,847

[22] Filed: Nov. 13, 1986

[30] Foreign Application Priority Data

Dec. 20, 1985 [JP] Japan .................. 60-289039

[51] Int. Cl.$^4$ .............. C07D 409/14; A61K 31/47
[52] U.S. Cl. .................... 514/312; 546/156; 548/550; 548/551; 548/566; 548/568; 560/9; 560/51; 560/53
[58] Field of Search .............. 514/312; 546/156

[56] References Cited

U.S. PATENT DOCUMENTS 4,616,019 10/1986 Chu, II .................. 514/211
4,617,308 10/1986 Mich et al. .................. 546/156
4,730,000 3/1988 Chu .................. 514/254

FOREIGN PATENT DOCUMENTS 0154780 9/1985 European Pat. Off. ............ 514/312

OTHER PUBLICATIONS

Chemical Abstracts, vol. 106, 119709k for Japan Pat. No. 61,251,667 (8/11/86).

*Primary Examiner*—Donald G. Daus
*Assistant Examiner*—E. Bernhardt
*Attorney, Agent, or Firm*—Wegner & Bretschneider

[57] ABSTRACT

Novel 1-thienyl-4-oxoquinoline-3-carboxylic acid compounds of the formula

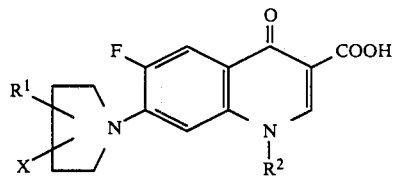

wherein $R^1$ is an amino (lower) alkyl, $R^2$ is thienyl, and X is a halogen atom, and a pharmaceutically acceptable salt thereof, said compounds having excellent antimicrobial activity and hence being useful as an antimicrobial agent, and a pharmaceutical composition comprising as an active ingredient said 1-thienyl-4-oxoquinoline-3-carboxylic acid compounds or a pharmaceutically acceptable salt thereof in admixture with a pharmaceutically acceptable diluent or carrier.

2 Claims, No Drawings

ANTIMICROBIAL 1-THIENYL-4-OXOQUINOLINE-3-CARBOXYLIC ACIDS

The present invention relates to novel antimicrobial benzoheterocyclic compounds and salts thereof, more particularly 1-thienyl-4-oxoquinoline-3-carboxylic acid compounds of the formula:

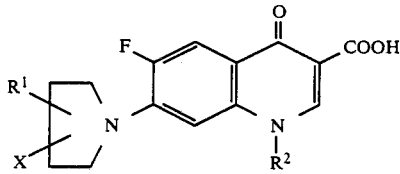

wherein $R^1$ is an amino (lower) alkyl, $R^2$ is thienyl, and X is a halogen atom, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

Prior art

European Patent Publication No. 0131839 discloses the following compounds:

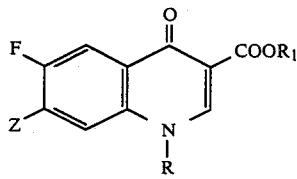

wherein $R_1$ is hydrogen or a carboxy protecting group, R is a substituted or unsubstituted aromatic heterocyclic ring including thiophene, Z is a substituted or unsubstituted aliphatic heterocyclic ring including pyrrolidine, but does not specifically disclose the specific 1-thienyl-4-oxoquinoline-3-carboxylic acid compounds [1] of the present invention.

BRIEF DESCRIPTION OF THE INVENTION

The object of the present invention is to provide novel benzoheterocyclic compounds of the formula [1]and salts thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the specification, the term "lower alkyl" includes straight chain or branched chain $C_1-C_6$ alkyl groups, such as methyl, ethyl, propyl, isopropyl, butyl, sec-butyl, tert-butyl, pentyl, hexyl, etc.

The term "amino (lower) alkyl" includes aminoalkyl groups in which alkyl moiety is a straight chain or branched chain $C_1-C_6$ alkyl group as mentioned above, such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, etc.

The term "halogen atom" includes fluorine, chlorine, bromine or iodine atom.

The group

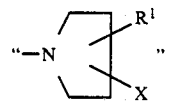

includes 1-pyrrolidinyl groups bearing the above "amino (lower) alkyl" and "halogen atom" as substituents, such as 3-aminomethyl-4-chloropyrrolidinyl, 3-aminomethyl-2-chloropyrrolidinyl, 3-aminomethyl-5-fluoropyrrolidinyl, 3-aminomethyl-4-fluoropyrrolidinyl, 3-aminomethyl-4-bromopyrrolidinyl, 3-(2-aminoethyl)-4-chloropyrrolidinyl, 2-(1-aminoethyl)-4-iodopyrrolidinyl, 2-(4-aminobutyl)-4-chloropyrrolidinyl, 3-aminomethyl-5-chloropyrrolidinyl, 3-(5-aminopentyl)-2-fluoropyrrolidinyl, 4-(2-aminoethyl)-3-bromopyrrolidinyl, 2-(3-aminopropyl)-3-chloropyrrolidinyl, 2-(6-aminohexyl)5-fluoropyrrolidinyl, 3-aminomethyl-4-fluoropyrrolidinyl, 4-(3-aminopropyl)-2-bromopyrrolidinyl, 3-(1,1-dimethyl-2-aminoethyl)-4-chloropyrrolidinyl, etc.

The term "lower alkanoyl" includes straight chain or branched chain $C_1-C_6$ alkanoyl groups, such as formyl, acetyl, propionyl, butyryl, isobutyryl, pentanoyl, hexanoyl, etc.

The term "lower alkoxy" includes straight chain or branched chain $C_1-C_6$ alkoxy groups, such as methoxy, ethoxy, propoxy, isopropoxy, butoxy, sec-butoxy, tert-butoxy, pentyloxy, hexyloxy, etc.

The term "lower alkanoylamino (lower) alkyl" includes alkanoylaminoalkyl groups in which alkanoyl moiety is a straight chain or branched chain $C_1-C_6$ alkanoyl group and alkyl moiety is a straight chain or branched chain $C_1-C_6$ alkyl group, such as formylaminometyl, acetylaminomethyl, 2-(propionylamino)ethyl, 1-(butyrylamino)ethyl, 3-(pentanoylamino)propyl, 4-(hexanoylamino)butyl, 5-(acetylamino)pentyl, 6-(propionylamino)hexyl, 1,1-dimethyl-2-(acetylamino)ethyl, 2-methyl-3-(acetylamino)propyl, etc.

The term "α-phenyl (lower) alkyl" includes α-phenylalkyl groups in which alkyl moiety is a straight chain or branched chain $C_1-C_6$ alkyl groups, such as benzyl, α-phenethyl, etc.

The term "lower alkylene" includes straight chain or branched chain $C_1-C_6$ alkylene groups, such as methylene, ethylene, trimethylene, tetramethylene, pentamethylene, hexamethylene, methylmethylene, 1,1-dimethylethylene, 2,2-dimethyltrimethylene, etc.

The term "lower alkanesulfonyl" includes methanesulfonyl, ethanesulfonyl, propanesulfonyl, isopropanesulfonyl, butanesulfonyl, tert-butanesulfonyl, pentanesulfonyl, hexanesulfonyl, or the like.

The term "arylsulfonyl" includes phenylsulfonyl, 4-methylphenylsulfonyl, 2-methylphenylsulfonyl, 4-nitrophenylsulfonyl, 4-methoxyphenylsulfonyl, 3-chlorophenylsulfonyl, α-naphthylsulfonyl, or the like.

The term "aralkylsulfonyl" includes benzylsulfonyl, 2-phenylethylsulfonyl, 4-phenylbutylsulfonyl, 4-methylbenzylsulfonyl, 2-methylbenzylsulfonyl, 4-nitrobenzylsulfonyl, 4-methoxybenzylsulfonyl, 3-chlorobenzylsulfonyl, α-naphthylmethylsulfonl, or the like.

The compounds [1] and their salts of the present invention can be prepared by various processes, for example, by the process as shown in the following reaction scheme-I

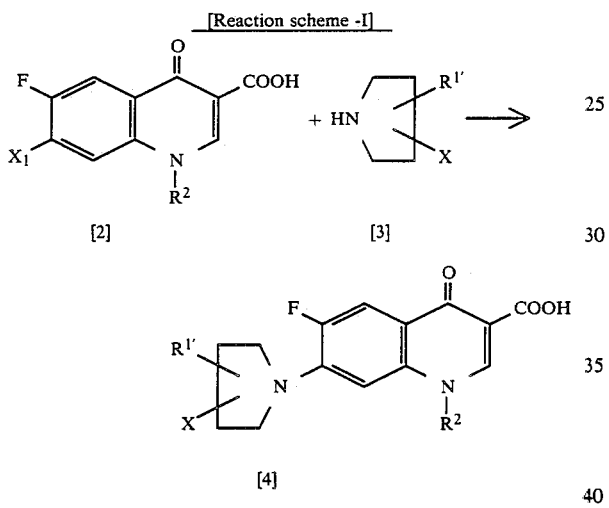

wherein $R^2$ and X are as defined above, $R^{1'}$ is an amino (lower) alkyl or lower alkanoylamino (lower) alkyl, and $X^1$ is a halogen atom.

The reaction of the compound [2] and the compound [3] is carried out in a solvent, wherein both compounds are used in a wide range of ratio, and the compound [3] is usually used in an amount of at least 1 mole, preferably 1 to 5 moles, per 1 mole of the compound [2]. The solvent includes water, alcohols (e.g. methanol, ethanol, isopropanol, butanol, amyl alcohol, isoamyl alcohol, etc.), aromatic hydrocarbons (e.g. benzene, toluene, xylene, etc.), ethers (e.g. tetrahydrofuran, dioxane, diglyme, etc.), dimethylformamide (DMF), dimethyl sulfoxide (DMSO), hexamethylphosphoramide (HMPA), N-methyl-pyrrolidone, or the like. Among these solvents, the preferred one is DMF, DMSO, HMPA, and N-methylpyrrolidone. The reaction may also be carried out in the presence of an acid-removing agent, such as inorganic carbonates (e.g. sodium carbonate, potassium carbonate, sodium hydrogen carbonate, potassium hydrogen carabonate, etc.) or tertiary amines (e.g. pyridine, quinoline, triethylamine, etc.). The reaction is usually carried out under a pressure of from 1 to 20 atm., preferably from 1 to 10 atm., at a temperature of from 100° to 250° C., preferably 100° to 200° C., for 0.5 to 20 hours.

Among the compounds of the formula [4] in the above reaction scheme-I, the compound wherein $R^{1'}$ is an amino (lower) alkyl is a compound of the present invention. The compounds of the formula [4] wherein $R^{1'}$ is a lower alkanoylamino (lower) alkyl can be converted into the corresponding compound of the present invention [i.e. $R^{1'}$ is an amino (lower) alkyl] by hydrolysis thereof.

The hydrolysis is carried out in a suitable solvent in the presence of an acid or a basic compound. The solvent includes water, alcohols (e.g. methanol, ethanol, isopropanol, etc.), ethers (dioxane, tetrahydrofuran, etc.), and a mixture thereof. The acid includes mineral acids (e.g. hydrochloric acid, sulfuric acid, hydrobromic acid, etc.) and the basic compound includes metal hydroxides (e.g. sodium hydroxide, potassium hydroxide, calcium hydroxide, etc.), metal carbonates or hydrogen carbonates (e.g. potassium carbonate, sodium carbonate, sodium hydrogen carbonate, etc.). The reaction is usually carried out at a temperature of from 0° to 150° C., preferably from room temperature to 100° C., for 10 minutes to 15 hours.

In the reaction scheme-I, the compounds of the formulae [2] and [3] are novel or known compouds, which can be prepared by various processes, for example, by the precesses as shown in the following reaction schemes-II and -III.

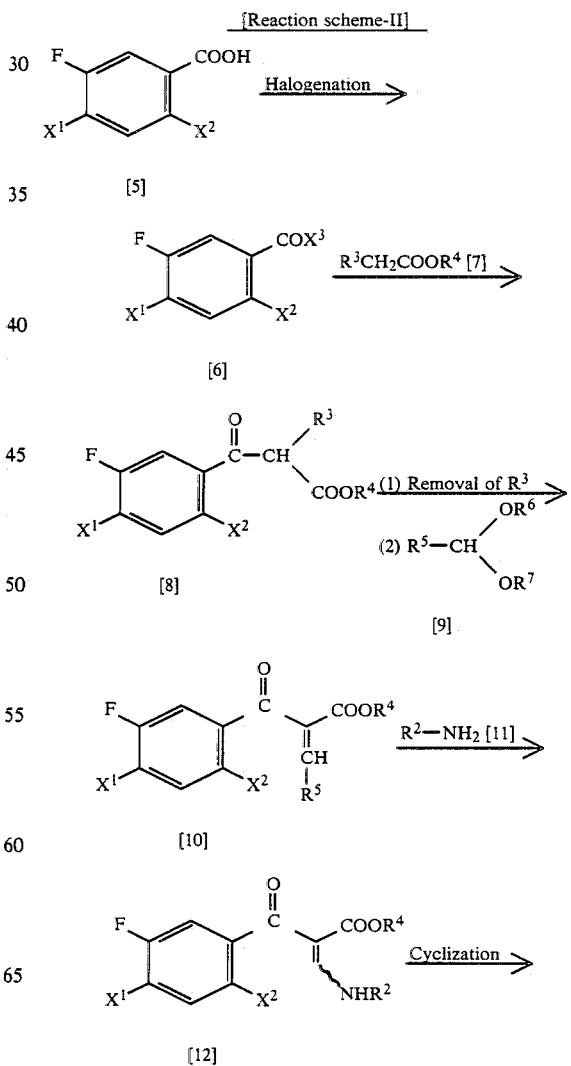

-continued
[Reaction scheme-II]

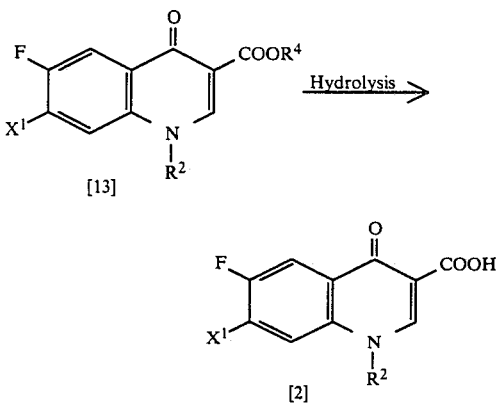

wherein $R^2$ and X are as defined above, $R^3$ is a group of the formula: $—COR^8$ (wherein $R^8$ is a lower alkyl) or a group of the formula: $—COOR^9$ (wherein $R^9$ is a lower alkyl), $R^4$ is a lower alkyl, $R^5$ is a group of the formula

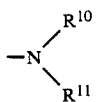

(wherein $R^{10}$ and $R^{11}$ are each a lower alkyl) or a lower alkoxy, $X^2$ and $X^3$ are each a halogen atom, $R^6$ and $R^7$ are each a lower alkyl.

The halogenation of the compound [5] is carried out by reacting with a halogenating agent in the presence or absence of a solvent. The solvent includes aromatic hydrocarbons (e.g. benzene, toluene, xylene, etc.), halogenated hydrocarbons (e.g. dichloromethane, chloroform, carbon tetrachloride, etc.), ethers (e.g. dioxane, tetrahydrofuran, diethyl ether, etc.), DMF, DMSO, and the like. The halogenating agent may be any conventional halogenating agents which can convert hydroxy in carboxy group into a halogen atom, and includes, for example, thionyl chloride, phosphorus oxychloride, phosphorus oxybromide, phosphorus pentachloride, phosphorus pentabromide, and the like. The amounts of the compound [5] and the halogenating agent are not specified, but, in case of using no solvent, the halogenating agent is usually used in a large excess amount, and in case of using a solvent, the halogenating agent is usually used in an amount of at least 1 mole, preferably 2 to 4 moles, per 1 mole of the compound [5]. The reaction temperature and the reaction period of time are not specified, either, but the reaction is usually carried out at a temperature of from room temperature to 100° C. for 30 minutes to 6 hours.

The reaction of the compound [6] and the compound [7] is carried out in a suitable solvent in the presence of a basic compound. The solvent may be any conventional solvents unless they give any undesirable effect on the reaction, and includes, for example, water, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, HMPA, etc.), and a mixture of these solvents. The basic compound includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), and organic bases (e.g. pyridine, piperidine, quinoline, triethylamine, N,N-dimethylaniline, etc.). The reaction is usually carried out at a temperature of from 0° to 150° C., preferably from room temperature to 120° C., for 0.5 to 15 hours. The compound [7] is usually used in an amount of at least 1 mole, preferably 1 to 2 moles, per 1 mole of the compound [6]. The basic compound is usually used in an amount of at least 1 mole, preferably 1 to 2 moles, per 1 mole of the compound [6].

The compound [8] wherein $R^3$ is the group: $—COR^8$ is subjected to the reaction for removal of the group: $—COR^8$ in a suitable solvent in the presence of a basic compound. The solvent includes ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. DMF, DMSO, HMPA, etc.), and the like. The basic compound includes ammonia gas, aqueous ammonia, ammonium salts (e.g. ammonium chloride, etc.), primary or secondary amines (e.g. ethylamine, diethylamine, piperidine, etc.), and the like. The reaction is usually carried out at a temperature of from 0° to 150° C., preferably from room temperature to 100° C., for 1 to 20 hours.

The compound [8] wherein $R^3$ is a group: $—COOR^9$ is subjected to the reaction for removal of the group: $—COOR^9$ in an aqueous solution in the presence of an acid catalyst. The acid catalyst includes mineral acids (e.g. hydrochloric acid, sulfuric acid, etc.) and organic acids (e.g. p-toluenesulfonic acid, etc.). The reaction is usually carried out at a temperature of from 0° to 150° C., preferably from room temperature to 100° C., for 1 to 20 hours.

The reaction of the $R^3$ group-removed compound and the compound [9] is carried out in a suitable solvent. The solvent may be any solvents which are used in the above reaction for the removal of the $R^3$ group. The reaction is usually carried out at a temperature of from 0° to 150° C., preferably from 0° to 100° C., for 0.5 to 10 hours. The comound [9] is usually used in an equimolar to large excess amount, preferably 1 to 2 moles per 1 mole of the compound [8]. In case of using a compound [9] wherein $R^5$ is a lower alkoxy group, the reaction may also be carried out by using acid anhydrides (e.g. acetic anhydride) as a solvent as well as above-mentioned solvents at a temperature of from 0° to 200° C., preferably 0° to 170° C.

The reaction of the compound [10] and the compound [11] is carried out in a suitable solvent. The solvent may be any conventional solvents unless they give any undesirable effect on the reaction, and includes, for example, alcohols (e.g. methanol, ethanol, propanol), ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The reaction is usually carried out at a temperature of from 0° to 150° C., preferably from room temperature to 100° C., for 0.5 to 15 hours. The compound [11] is usually used in an amount of at least 1 mole, preferably 1 to 2 moles, per 1 mole of the compound [10].

The cyclization of the compound [12] is carried out in a suitable solvent in the presence of a basic compound. The solvent may be any conventional solvents unless they give any undesirable effect on the reaction, and includes, for example, ethers (e.g. diethyl ether, dioxane, tetrahydrofuran, monoglyme, diglyme, etc.), aliphatic hydrocarbons (e.g. n-hexane, heptane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The basic compound includes inorganic bases (e.g. metallic sodium, metallic potassium, sodium hydride, sodium amide, sodium hydroxide, potassium hydroxide, etc.), metal alcoholates (e.g. sodium methylate, sodium ethylate, etc.), and organic bases (e.g. 1,8-diazobicyclo[5.4.0]undecene-7 (DBU), N-benzyltrimethylammonium hydroxide, tetrabutylammonium hydroxide, etc.). The reaction is usually carried out at a temperature of from 0° to 150° C., preferably from room temperature to 120° C., for 0.5 to 5 hours. The basic compound is usually used in an amount of at least 1 mole, preferably 1 to 2 moles, per 1 mole of the compound [12].

The hydrolysis of the compound [13] can be carried out under the conditions of conventional hydrolysis, for instance, in the presence of a basic compound (e.g. sodium hydroxide, potassium hydroxide, barium hydroxide, etc.), a mineral acid (e.g. sulfuric acid, hydrochloric acid, nitric acid, hydrobromic acid, etc.) or an organic acid (e.g. acetic acid, aromatic sulfonic acids, etc.) in a solvent such as water, alcohols (e.g. methanol, ethanol, isopropanol, etc.), ketones (e.g. acetone, methyl ethyl ketone, etc.), ethers (e.g. dioxane, ethylene glycol, etc.), acetic acid, or a mixture thereof. The reaction is usually carried out at a temperature of from room temperature to 200° C., preferably 50° to 150° C., for 0.5 to 6 hours. By the reaction, there is produced the compound [2].

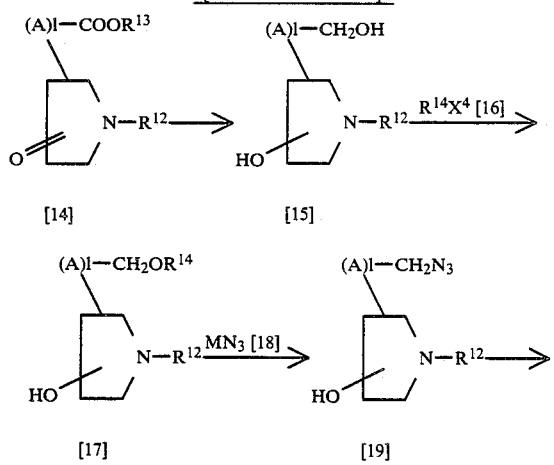

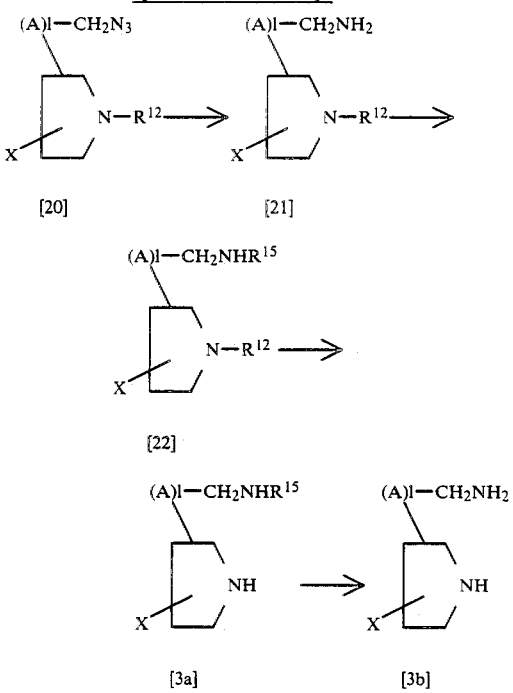

wherein $R^{12}$ is a α-phenyl (lower) alkyl, $R^{13}$ is a lower alkyl, A is a lower alkylene, l is 0 or 1, $R^{14}$ is a lower alkanesulfonyl, arylsulfonyl or aralkylsulfonyl, $R^{15}$ is a lower alkanoyl, $X^4$ is a halogen atom, M is a alkaline metal such as sodium or potassium, and X is as defined above.

The reduction of the compound [14] is carried out in the presence of a suitable reducing agent for hydrogenation. The reducing agent includes, for example, sodium aluminum hydride, lithium aluminum hydride, sodium borohydride, diborane, and the like, and is usually used in an amount of at least 1 mole, preferably 1 to 3 moles, per 1 mole of the compound [14]. In case of lithium aluminum hydride, it is preferably used in an equimolar amount to the compound [14]. The reduction reaction is usually carried out in a suitable solvent, for example, water, alcohols (e.g. methanol, ethanol, isopropanol, etc.), ethers (e.g. tetrahydrofuran, diethyl ether, diglyme, etc.), or the like, at a temperature of −60° to 50° C., preferably −30° C. to room temperature, for 10 minutes to 20 hours. In case of using lithium aluminum hydride or diborane as a reducing agent, an anhydrous solvent such as diethyl ether, tetrahydrofuran or diglyme is preferably employed.

The reaction of the compound [15] and the compound [16] is carried out in a suitable solvent in the presence of a basic compound. The solvent includes halogenated hydrocarbons (e.g. dichloromethane, chloroform, carbon tetrachloride, etc.), aromatic hydrocarbons (e.g. benzene, toluene, xylene etc.), ethers (e.g. diethyl ether, tetrahydrofuran, dioxane, etc.), and the like. The basic compound includes inorganic bases (e.g. sodium hydroxide, potassium carbonate, sodium hydrogen carbonate, potassium hydrogen carbonate, etc.), and organic bases (e.g. triethylamine, N,N-dimethylaniline, piperidine, pyrrolidine, etc.). The reaction is usually carried out at a temperature of from −50° C. to room temperature, preferably from −30° to 0° C., for 10 minutes to 5 hours. The compound [16] is usually used in an amount of 1 to 1.5 moles per 1 mole of the compound [15].

The reaction of the compound [17] and the compound [18] is carried out in a suitable solvent in the presence or absence of a basic compound. The solvent includes, for example, water, halogenated hydrocarbons (e.g. dichloromethane, chloroform, carbon tetrachloride, etc.), aromatic hydrocarbons (e.g. benzene, toluene, xylene, etc.), ethers (e.g. diethyl ether, tetrahydrofuran, dioxane, etc.), esters (e.g. methyl acetate, ethyl acetate, etc.), aprotic polar solvents (e.g. DMF, DMSO, HMPA, etc.), alcohols (e.g. methanol, ethanol, isopropanol, etc.), acetone, acetonitrile, and a mixture thereof. The basic compound includes the basic compounds employed in the reaction of the compound [15] and the compound [16]. The reaction is usually carried out at a temperature of from −30° to 180° C., preferably from 0° to 150° C., for 5 minutes to 30 hours. The compound [18] is usually used in an amount of at least 1 mole, preferably 1 to 1.5 moles, per 1 mole of the compound [17].

The halogenation of the compound [19] can be carried out under a reaction condition usually employed in halogenation of a hydroxyl group, for example, by reacting the compound with a halogenating agent in the presence or absence of a suitable inert solvent. The halogenating agent includes, for example, hydrohalogenic acids (e.g. hydrochloric acid, hydrobromic acid, etc.), N,N-diethyl-1,2,2-trichlorovinylamide, phosphorus pentachloride, phosphorus pentabromide, phosphorus oxychloride, thionyl chloride, and the like. The inert solvent includes ethers (e.g. dioxane, tetrahydrofuran, etc.), halogenated hydrocarbons (e.g. chloroform, dichloromethane, carbon tetrachloride, etc.), and the like. The halogenating agent is used in an amount of at least 1 mole, usually in an excess amount, per 1 mole of the compound [19]. The reaction is usually carried out at a temperature of from room temperature to 150° C., preferably from room temperature to 80° C., for 1 to 6 hours.

The reduction of the compound [20] is usually carried out by a catalytic reduction in the presence of a suitable reduction catalyst. The reduction catalyst includes catalysts usually used for a catalytic reduction, for example, platinum, platinum oxide, palladium black, palladium carbon, Raney nickel and the like. The reduction catalyst may be usually used in an amount of from 0.1 to 0.5-fold by weight of the compound [20]. The catalytic reduction is carried out by shaking well in a solvent, for example, water alcohols (e.g. methanol, ethanol, isopropanol, etc.), ethers (e.g. tetrahydrofuran, diethyl ether, etc.), and the like, under a hydrogen pressure of from 1 to 10 atom., preferably from 1 to 5 atom., at a temperature of from −30° C. to boiling point of a solvent employed, preferably from 0° to 70° C.

The reaction of converting the compound [21] into the compound [22] is carried out by reacting the compound [21] with an acylating agent of the formula: $R^{15}COX^4$ or $(R^{15}CO)_2O$ wherein $R^{15}$ and $X^4$ are as defined above, in the presence or absence of a basic compound. The basic compound includes alkali metals (e.g. metallic sodium, metallic potassium, etc.) and hydroxides, carbonates or hydrogen carbonates thereof, organic bases (e.g. pyridine, piperidine, etc.), and the like. The reaction is carried out in the presence or absence of a suitable solvent. The solvent includes ketones (e.g. acetone, methyl ethyl ketone, etc.), ethers (e.g. diethyl ether, dioxane, etc.), aromatic hydrocarbons (e.g. benzene, toluene, xylene, etc.), water, pyridine, and the like. The acylating agent is used in an amount of at least 1 mole, preferably 1 mole to a large excess amount, per 1 mole of the compound [21]. The reaction is carried out at a temperature of from 0° to 200° C., preferably from 0° to 150° C., for 0.5 to 20 hours.

The reduction of the compound [22] can be carried out under the same reaction condition as used in the reduction of the above compound [20].

The reaction of converting the compound [3a] into the compound [3b] can be carried out under the same reaction condition as used in the above-mentioned hydrolysis of the compound [4] wherein $R^{1'}$ is a lower alkanoylamino (lower) alkyl to convert into the compound [4] wherein $R^{1'}$ is an amino (lower) alkyl.

In the compounds of the present invention there are optical and geometrical isomers, and the present invention includes also these isomers.

The compounds [1] can easily be converted into a salt thereof by treaing them with a pharmaceutically acceptable acid or base. The acid includes inorganic acids (e.g. hydrochloric acid, sulfuric acid, phosphoric acid, hydrobromic acid, etc.) and organic acids (e.g. succinic acid, maleic acid, fumaric acid, malic acid, tartaric acid, citric acid, lactic acid, benzoic acid, etc.). The base includes sodium hydroxide, potassium hydroxide, calcium hydroxide, sodium carboante, potasium hydrogen carbonate, and the like.

The compound thus obtained can easily be isolated by conventional methods, such as extraction with solvents, dilution method, recrystallization, column chromatography, preparative thin layer chromatography, and the like.

The compounds [1] of the present invention or salts thereof show particularly excellent antimicrobial activity against gram positive bacteria such as *Staphylococcus aureus, Streptococcus faecalis* or *Bacillus subtilis* and also show excellent antimicrobial activity against anaerobic bacteria or various fresh clinically isolated strains, and hence, are useful as an antimicrobial agent for the treatment of diseases induced by these microorganisms. These compounds show also low toxicity and less side effect and are characteristic in good absorbability and in sustained activity. Moreover, the compounds are highly excreted via urine and hence are useful for the treatment of urinary infectious diseases, and further because of easy excretion via bile, they are also useful for the treatment of intestinal infectious diseases.

The compounds of the present invention are usually used in the form of a usual pharmaceutical preparation. The pharmaceutical preparation can be prepared in admixture with conventional pharmaceutically acceptable diluents or carriers, such as fillers, weighting agents, binding agents, wetting agents, disintegrators, surfactants, rublicating agents, and the like. The pharmaceutical preparation includes various preparations suitable for treatment of the diseases, for example, tablets, pills, powders, solutions, suspensions, emulsions, granules, capsules, suppositories, injections (solutions, suspensions, etc.), and the like. In the preparation of tablets, there may be used any conventional carriers, for example, vehicles (e.g. lactose, white sugar, sodium chloride, glucose, urea, starches, calcium carbonate, kaolin, crystalline cellulose, silicate, etc.), binding agents (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), rublicants (e.g. purified talc, stearates, boric acid powder, polyethylene glycol, etc.), and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carries, such as vehicles (e.g. glucose, lactose, starches, cacao butter, hydrogenated vegetable oils, kaolin, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semi-synthetized glycerides, and the like. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, ethyl alcohol, propylene glycol, ethoxylated isostearyl alcohol, polyoxylated isostearyl alcohol, polyoxyethylene sorbitan fatty acid esters, and the like. The preparations may also be incorporated with sodium chloride, glucose or glycerin in an amount sufficient to make them isotonic with the body liquid. The preparations may also be incorported with conventional solubilizers, buffering agents, anesthetizing agents, and further, with coloring agents, presevatives, perfumes, flavors, sweeting agents, and other medicaments. The preparations in the form of a paste, cream or gel may be prepared by using as a diluent white vaseline, paraffin, glycerin, cellulose derivatives, polyethylene glycol, silicone, bentonite, or the like.

The active compounds [1] or salts thereof maybe contained in any amount in the preparations, and are usually contained in an amount of 1 to 70 % by weight based on the whole weight of the preparations.

The pharmaceutical preparations of the present invention can be administered in any methods. Suitable method for administration may be selected in accordance with the preparation form, age and sex of the patients, degree of severity of the diseases, and the like. For instance, tablets, pills, solutions, suspensions, emulsions, granules and capsules are administered in oral route. In case of injection, it is administered intravenously alone or together with an auxiliary liquid (e.g. glucose, amino acid solution). The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of the patients, severity of the diseases, and the like, but is usually in the range of about 0.2 to 100 mg of the active compound [1] or a salt thereof per 1 kg of body weight of the patient per day. The preparation is usually administered by dividing into 2 to 4 times per day.

The present invention is illustrated by the following Reference Examples, Examples, Preparations, and Experiments.

REFERENCE EXAMPLE 1

Thionyl chloride (70 ml) is added to 2-bromo-4,5-difluorobenzoic acid (39.5 g), and the mixture is allowed to stand at room temperature for one hour and then refluxed for one hour. After completion of the reaction, the excess thionyl chloride is distilled off under reduced pressure. The oily residue is distilled under reduced pressure to give 2-bromo-4,5-difluorobenzoyl chloride (37.8 g) as a pale yellow oily substance, b.p. 121°–123° C. (32 mmHg).

REFERENCE EXAMPLE 2

Magnesium ribbon (7.3 g) is suspended in absolute ethanol (15 ml), and thereto is added carbon tetrachloride (1.5 ml), and thereto is added dropwise a mixture of diethyl malonate (48 g), absolute ethanol (30 ml) and anhydrous ether (120 ml) over a period of one hour. After the addition, the mixture is refluxed for 2 hours. After cooling till room temperature, a solution of 2-bromo-4,5-difluorobenzoyl chloride (92 g) in anhydrous ether (50 ml) is added dropwise to the mixture. After the addition, the mixture is allowed to stand overnight at room temperature. A mixture of ice-water (120 ml) and conc. sulfuric acid (8 ml) is added dropwise to the reaction mixture under ice-cooling. After the addition, the mixture is extracted with ether. The ether layer is washed with saturated aqueous sodium chloride solution and dried over magnesium sulfate. The solvent is distilled off under reduced pressure to give diethyl (2-bromo-4,5-difluorobenzoyl)malonate (123 g).

REFERENCE EXAMPLE 3

To a solution of diethyl (2-bromo-4,5-difluorobenzoyl)malonate (75.6 g) in water (100 ml) is added p-toluenesulfonic acid (0.3 g), and the mixture is refluxed for 3 hours. After cooling, the reaction mixture is extracted with dichloromethane. The dichloromethane layer is washed with saturated aqueous sodium chloride solution and dried over magnesium sulfate. After distilling off the solvent under reduced pressure, the residue is distilled to give ethyl (2-bromo-4,5-difluorobenzoyl)acetate (52.0 g), b.p. 105°–115° C. (0.15 mmHg).

REFERENCE EXAMPLE 4

A mixture of ethyl (2-bromo-4,5-difluorobenzoyl)acetate (52.0 g), ethyl orthoformate (36.6 g) and acetic anhydride (41.6 g) is heated at 150° C. for 2 hours. After the reaction, the reaction mixture is concentrated under reduced pressure. The resulting residue is purified by silica gel column chromatography (solvent, dichloromethane: n-hexane =2:1) to give ethyl 2-(2-bromo-4,5-difluorobenzoyl)-3-ethoxyacrylate (49 g).

REFERENCE EXAMPLE 5

To a solution of ethyl 2-(2-bromo-4,5-difluorobenzoyl)-3-ethoxyacrylate (1.1 g) in ethanol (10 ml) is added portionwise 2-aminothiophene (0.3 g). After stirring the mixture at room temperature for 30 minutes, the precipitated crystals are separated by filtration to give ethyl 2-(2-bromo-4,5-difluorobenzoyl)-3-(2-thienyl)acrylate (0.9 g).

REFERENCE EXAMPLE 6

Ethyl 2-(2-bromo-4,5-difluorobenzoyl)-3-(2-thienyl)acrylate (0.9 g) is dissolved in anhydrous dioxane (10 ml), and thereto is added portionwise 60% sodium hydride (0.1 g) at room temperature. After the addition, the mixture is stirred at room temperature for 30 minutes and then heated at 100° C. for 30 minutes. After allowing to cool, the reaction mixture is poured into saturated aqueous ammonium chloride, and extracted with dichloromethane. The dichloromethane layer is dried over magnesium sulfate and the solvent is then distilled off under reduced pressure to give 6,7-difluoro-1-(2-thienyl)-1,4-dihydro-4-oxoquinoline-3-carboxylate (0.6 g).

NMR (CDCl$_3$)$\delta$:8.51 (1H,s), 8.20 (1H,dd,J=9Hz, 10.5Hz), 7.52 (1H,dd,J=2Hz,4.5Hz), 7.10–7.36 (2H,m), 6.93 (1H,dd,J=6Hz,12Hz), 4.36 (2H,q,J=7Hz), 1.37 (3H,t,J=7Hz).

REFERENCE EXAMPLE 7

To ethyl 6,7-difluoro-1-(2-thienyl)-1,4-dihydro-4-oxoquinoline-3-carboxylate (0.6 g) are added 90% acetic acid (3 ml) and conc. hydrochloric acid (0.8 ml), and the mixture is refluxed for one hour. After allowing to cool, the precipitated crystals are separated by filtration, and washed with water, ethanol and ether in this order to give 6,7-difluoro-1-(2-thienyl)-1,4-dihydro-4-oxoquinoline-3-carboxylic acid (0.4 g) as colorless crystals, m.p. 245°–246° C.

REFERENCE EXAMPLE 8

6,7-Difluoro-1-(2-thienyl)-1,4-dihydro-4-oxoquinoline-3-carboxylic acid (0.5 g) and 3-acetylaminomethyl-4-chloropyrrolidine (0.86 g) are added to N-methylpyrrolidone (50 ml) and the mixture is stirred at 110° C. for one hour. After the reaction, the solvent is distilled off and the resulting residue is crystallized with ethanol. The crystals are separated by filtration and then recrystallized from ethanol to give 6-fluoro-1-(2-thienyl)7-(3-acetylaminomethyl-4-chloro-1-pyrrolidinyl)-1,4-dihydro-4-oxoquinoline-3-carboxylic acid (0.54 g) powder, m.p. 145° C. (decomp.).

REFERENCE EXAMPLE 9

To a solution of 1-benzyl-3-ethoxycarbonyl-4-oxypyrrolidine (20.4 g) in methanol (200 ml) is added portionwise sodium borohydride (18.9 g) with stirring under ice-cooling. The mixture is stirred overnight at room temperature and then concentrated. To the resulting residue is added water (100 ml), and the mixture is allowed to stand for one hour and then extracted with chloroform. After concentrating the chloroform layer, 10% hydrochloric acid (80 ml) is added to the residue and the mixture is allowed to stand for one hour. Then, the mixture is strongly alkalified with an aqueous sodium hydroxide and again extracted with chloroform. The chloroform layer is dried and concentrated, and the residue is distilled to give 1-benzyl-3-hydroxymethyl-4-hydroxypyrrolidine (10.7 g) as an yellow oil, b.p. 160°–167° C. (0.2 mmHg).

NMR (CDCl$_3$)$\delta$:2.00–3.00 (4H,m), 3.44 (2H,brs), 3.47–3.84 (5H,m), 4.00–4.54 (1H,m), 7.27 (5H,s).

REFERENCE EXAMPLE 10

1-Benzyl-3-hydroxymethyl-4-hydroxypyrrolidine (66.2 g) and triethylamine (38.8 g) are added to dry dichloromethane (700 ml) and the mixture is cooled till a temperature of from −5° to −10° C. At this temperature, methanesulfonyl chloride (36.6 g) is added dropwise to the mixture with stirring. After the addition, the mixture is stirred for 30 minutes, and then washed with an aqueous sodium hydrogen carbonate and subsequently with water. Thereafter, the dichloromethane layer is separated, dried and concentrated to give 1-benzyl-4-hydroxy-3-methanesulfonylmethylpyrrolidine (80.8 g) as an oil.

NMR (CDCl$_3$)$\delta$:2.20–3.10 (5H,m), 2.98, 3.02 (3H,s), 3.57–3.70 (2H,m), 4.00–4.40 (3H,m), 7.30 (5H,brs).

REFERENCE EXAMPLE 11

1-Benzyl-4-hydroxy-3-methanesulfonylmethylpyrrolidine (80.8 g) is added to methanol-water (3:2) (1 liter), and thereto is added dropwise sodium azide (24.5 g), and the mixture is refluxed for 24 hours. After the reaction, the mixture is concentrated and extracted with dichloromethane. The dichloromethane solution is washed with water and saturated saline, dried and concentrated to give 1-benzyl-4-hydroxy-3-azidomethylpyrrolidine (59.7 g) as an oil.

NMR (CDCl$_3$)$\delta$:1.98–3.13 (6H,m), 3.34 (2H,d,J=7Hz), 3.55–3.70 (2H,m), 3.90–4.10, 4.17–4.43 (1H,m), 7.28 (5H,brs).

IR (Neat) cm$^{-1}$: 3368, 2098.

REFERENCE EXAMPLE 12

1-Benzyl-4-hydroxy-3-azidomethylpyrrolidine (59.7 g) is added to chloroform (100 ml), and the mixture is saturated with dry hydrogen chloride gas. A solution of thionyl chloride (61.2 g) in chloroform (100 ml) is added dropwise to the mixture under reflux. After refluxing for 2 hours, the mixture is concentrated. To the residue is added ethanol and the excess thionyl chloride is removed, and then, the mixture is again concentrated. After neutralizing the concentrate with an aqueous sodium hydrogen carbonate, the mixture is extracted with dichloromethane. The dichloromethane layer is washed with water, dried and concentrated, and the resulting residue is then purified by silica gel column chromatography (solvent, ethyl acetate-n-hexane) to give 1-benzyl-3-azidomethyl-4-chloropyrrolidine (26.0 g) as an yellow oil.

NMR (CDCl$_3$)$\delta$:2.37–3.00 (4H,m), 3.17–3.70 (3H,m), 3.70 (2H,m), 4.35–4.58 (1H,m), 7.30 (5H,brs).

IR (Neat) cm.$^{-1}$2098.

REFERENCE EXAMPLE 13

To 1-benzyl-3-azidomethyl-4-chloropyrrolidine (3.0 g) are added ethanol (50 ml) and 10 % palladium carbon (0.5 g), and catalytic reduction is carried out under a hydrogen pressure of from 3 to 4 atm. at 50° C. After removing the catalyst from the mixture by a filteration, the resultant is concentrated to give 3-aminomethyl-1-benzyl-4-chloropyrrolidine (2.96g) as an oil.

NMR (CDCl$_3$)$\delta$:1.65 (2H,s), 2.27–3.47 (7H,m), 3.70 (2H,s), 4.40–4.67 (1H,m), 7.30 (5H,brs).

REFERENCE EXAMPLE 14

To 3-aminomethyl-1-benzyl-4-chloropyrrolidine (2.69 g) is added ethanol (50 ml) and thereto is added dropwise acetyl chloride (1.02 g) with stirring under ice-cooling. The mixture is stirred at room temperature overnight, then concentrated, neutralized with saturated aqueous sodium hydrogen carbonate, and extructed with dichloromethane. The dichloromethane layer is dried and concentrated to give 3-acetylaminomethyl-1-benzyl-4-chloropyrrolidine (2.50 g) as an yellow oil.

NMR (CDCl$_3$)δ:1.96 (3H,s), 2.37–3.77 (7H,m), 3.67 (2H,s), 4.33–4.57 (1H,m), 5.77–6.20 (1H,m), 7.30 (5H,brs).

REFERENCE EXAMPLE 15

To 3-acetylaminomethyl-1-benzyl-4-chloropyrrolidine (2.5 g) are added ethanol (100 ml) and 10% palladium carbon (0.5 g), and catalytic reduction is carried out under a hydrogen pressure of from 3 to 4 atm. at a temperature of from 50° to 70° C. for 8 hours. After removing the catalyst from the mixture by a filteration, the resulting solution is concentrated to give 3-acetylamino-4-chloropyrrolidine (1.40 g) as a pale yellow oil.

NMR (CDCl$_3$)δ:1.99 (3H,s), 2.43–3.43 (8H,m), 4.33–4.57 (1H,m), 5.83–6.27 (1H,m).

EXAMPLE 1

To 6-fluoro-1-(2-thienyl)-7-(3-acetylaminomethyl-4-chloro-1-pyrrolidinyl)-1,4-dihydro-4-oxoquinoline-3-carboxylic acid (0.43 g) is added 20% hydrochloric acid (8 ml), and the mixture is refluxed for 5 hours. After cooling, the mixture is neutralized with saturated aqueous sodium hydrogen carbonate, the precipitated crystals are separated by filtration and dried. The product is converted into its hydrochloride by treating it with a hydrochloric acid-saturated ethanol, and the resulting crude crystals are recrystallized from ethanol-ether to give 6-fluoro-1-(2-thienyl)-7-(3-aminomethyl-4-chloro-1-pyrrolidinyl)-1,4-dihydro-4-oxoquinoline-3-carboxylic acid (0.35 g).

NMR (DMSO-d$_6$δ:2.70–4.40 (7H,m), 4.90–5.18 (1H,m), 6.18 (1H,d,J=8Hz), 7.13–8.80 (7H,m), 8.56 (1H,s).

IR (KBr)cm$^{-1}$: 1720 (s), 1630 (s), 1510 (s), 1460 (s).

PREPARATION 1

An injection preparation is prepared from the following components.

| Components | Amount |
| --- | --- |
| 6-Fluoro-1-(2-thienyl)-7-(3-aminomethyl-4-chloro-1-pyrrolidinyl)-1,4-dihydro-4-oxoquinoline-3-carboxylic acid | 200 mg |
| Glucose | 250 mg |
| Distilled water for injection | q.s. |
| Totally | 5 ml |

6-Fluoro-1-(2-thienyl)-7-(3-aminomethyl-4-chloro-1-pyrrolidinyl)-1,4-dihydro-4-oxoquinoline-3-carboxylic acid and glucose are dissolved in distilled water for injection, and the solution is added to a 5 ml ampoule, which is purged with nitrogen gas and then subjected to sterilization at 121° C. for 15 minutes to give an injection preparation.

Preparation 2

Film coated tablets are prepared from the following components.

| Components | Amount |
| --- | --- |
| 6-Fluoro-1-(2-thienyl)-7-(3-aminomethyl-4-chloro-1-pyrrolidinyl)-1,4-dihydro-4-oxo quinoline-3-carboxylic acid | 100 g |
| Avicel (tradename of microcrystalline cellulose, manufactured by Asahi Chemical, Japan) | 40 g |
| Corn starch | 30 g |
| Magnesium stearate | 2 g |
| TC-5 (tradename of hydroxypropyl methylcellulose, manufactured by Shinetsu Kagaku Kogyo, Japan) | 10 g |
| Polyethylene glycol 6000 | 3 g |
| Castor oil | 40 g |
| Ethanol | 40 g |

6-Fluoro-1-(2-thienyl)-7-(3-aminomethyl-4-chloro-1-pyrrolidinyl)-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

PREPARATION 3

An ointment is prepared from the following components.

| Components | Amount |
| --- | --- |
| 6-Fluoro-1-(2-thienyl)-7-(3-aminomethyl-4-chloro-1-pyrrolidinyl)-1,4-dihydro-4-oxoquioline-3-carboxylic acid | 2 g |
| Purified lanolin | 5 g |
| Bleached beeswax | 5 g |
| White vaseline | 88 g |
| Totally | 100 g |

Bleached beeswax is made liquid by heating, and thereto are added 6-fluoro-1-(2-thienyl)-7-(3-aminomethyl-4-chloro-1-pyrrolidinyl)-1,4-dihydro-4-oxoquinoline-3-carboxylic acid, purified lanolin and while vaseline, and the mixture is heated until it becomes liquid. The mixture is stirred until it is solidified to give an ointment.

Experiment (Antimicrobial activity in in vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of $1 \times 10^8$ cells/ml (O.D. 660 mμ, 0.07–0.16) and $1 \times 10^6$ cells/ml (100 folds dilution). The results are shown in Table 1.

TABLE 1

[Test compound]:
1. 6-Fluoro-1-(2-thienyl)-7-(3-aminomethyl-4-chloro-1-pyrrolidinyl)-1,4-dihydro-4-oxoquinoline-3-carboxylic acid

| | Test Compd. No. 1 | |
| --- | --- | --- |
| Test microorganisms | $1 \times 10^8$ | $1 \times 10^6$ |
| Staphylococcus aureus FDA 209P | 0.48 | 0.24 |
| Staphylococcus pyrogens IID S-23 | 0.781 | 0.195 |
| Streptococcus faecalis IFO 12580 | 0.39 | 0.195 |
| Bacillus subtilis ATCC 6633 | 0.024 | 0.012 |
| Escherichia coli NIHJ JC-2 | 0.024 | 0.024 |
| Escherichia coli No. 29 | 0.024 | 0.024 |
| Klebsiella pneumoniae NCTC 9632 | 0.048 | 0.024 |

TABLE 1-continued

[Test compound]:

1. 6-Fluoro-1-(2-thienyl)-7-(3-aminomethyl-4-chloro-1-pyrrolidinyl)-1,4-dihydro-4-oxoquinoline-3-carboxylic acid

| Test microorganisms | Test Compd. No. 1 | |
|---|---|---|
| | $1 \times 10^8$ | $1 \times 10^6$ |
| Proteus inconstans IFO 12930 | 1.56 | 0.781 |
| Proteus morganii IID Kono | 0.39 | 0.195 |
| Serratia marcescens IFO 12648 | 0.781 | 0.195 |
| Acinetobacter calcoaceticus AC-54 | 0.39 | 0.195 |
| Pseudomonas aeruginosa ATCC 10145 | 0.781 | 0.781 |
| Pseudomonas aeruginosa E-2 | 1.56 | 1.56 |

What is claimed is:

1. The compound 6-flouro-1-(2-thienyl)-7-(3-aminomethyl -4-chloro-1-pyrrolidinyl)-1,4-dihydro-4-oxoquinoline -3-carboxylic acid or a pharmaceutically acceptable salt thereof.

2. An anitmicrobial composition which comprises as an essential active ingredient an antimicrobially effective amount of 6-fluoro-1-(2-thienyl)-7-(3-aminomethyl-4-chloro-1-pyrrolikinyl)-1,4-dihydro-4-oxoquinoline-3-carboxylic acid or a pharmaceutically acceptable salt thereof in admixture with a pharmaceutically acceptable diluent or carrier.

* * * * *